US006270828B1

(12) United States Patent
DeBonte et al.

(10) Patent No.: US 6,270,828 B1
(45) Date of Patent: *Aug. 7, 2001

(54) CANOLA VARIETY PRODUCING A SEED WITH REDUCED GLUCOSINOLATES AND LINOLENIC ACID YIELDING AN OIL WITH LOW SULFUR, IMPROVED SENSORY CHARACTERISTICS AND INCREASED OXIDATIVE STABILITY

(75) Inventors: Lorin R. DeBonte, Delran, NJ (US); Willie H.-T. Loh, Philadelphia, PA (US); Fan Zhegong, Delran, NJ (US)

(73) Assignee: Cargill Incorporated, Wayzata, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/850,279

(22) Filed: May 5, 1997

Related U.S. Application Data

(60) Division of application No. 08/290,660, filed on Aug. 15, 1994, now Pat. No. 5,750,827, which is a continuation-in-part of application No. 08/140,205, filed on Nov. 12, 1993, now abandoned.

(51) Int. Cl.$^7$ ..................................................... A23D 7/00

(52) U.S. Cl. ............................................................. 426/601

(58) Field of Search .................................... 554/223, 224

(56) References Cited

U.S. PATENT DOCUMENTS

| 4,948,811 | * | 8/1990 | Spinner et al. | 514/560 |
|---|---|---|---|---|
| 4,948,881 | * | 8/1990 | Spinner et al. | 514/560 |
| 5,077,071 | | 12/1991 | Strop | 426/417 |
| 5,638,637 | * | 6/1997 | Wong et al. | 47/58 |

FOREIGN PATENT DOCUMENTS

| 0 289 183 | 11/1988 | (EP) . | |
|---|---|---|---|
| 0 323 753 | 7/1989 | (EP) | A01H/1/02 |
| WO 90/10380 | 9/1990 | (WO) . | |
| WO 92/03919 | 3/1992 | (WO) . | |

OTHER PUBLICATIONS

Grandis, "Stellar Low Linolenic–High Linoleic Acid Summer Rape", Can J. Plant Sci., 1988, 68:509–511.
Database, Theis, "New Methods for the Analysis of Rapeseed Constituents", No. XP–002089868, abstract only, 1976.
Database, Morice, "Contribution of Genetics and Selection to Improvement of Product and Product Quality of the Main Oilseeds in Temperate Countries", 1976, No. XP–002089869, abstract only.
Database, Khan et al., "Studies on the Physico–Chemical Characteristic of a New Genotype of Autumn", 1987, No. XP–002089870, abstract only.
Pleines et al., "Breeding for Improved C18–Fatty Acid Composition in Rapeseed (Brassica napus L.)", Fat Sci. Tech., 5:167–171, 1988.
Love et al., "Development of Low Glucosinolate Mustard", Can. J. Plant Sci., 70:419–424, 1990.
Choesin et al., "Allyl Isothiocyante Release and the Allelopathic Potential of Brassica Napus (Brassiaceae)", Amer. J. of Botany, 78(8):1083–1090, 1991.

(List continued on next page.)

Primary Examiner—Deborah D. Carr
(74) Attorney, Agent, or Firm—Fish & Richardson P.C.

(57) ABSTRACT

A canola line has been stabilized to produce seeds having an α-linolenic acid content of less than that of generic canola oil, more preferably less than or equal to about 7% α-linolenic acid relative to total fatty acid content of said seed and a total glucosinolate content of less than 18 μmol/g of defatted meal, more preferably less than or equal to about 15 μmol/g of defatted meal. This canola line has reduced sulfur content of less than or equal to 3.0 ppm, improved sensory characteristics and increased oxidative stability.

18 Claims, 10 Drawing Sheets

OTHER PUBLICATIONS

Lichter et al., "Glucosinolates Determined by HPLC in the Seeds of Microspore–Derived Homozygous Lines of Rapeseed (*Brassica napus* L.)", *Plant Breeding*, 100:209–221, 1988.

Abraham et al., "Removal of Sulfur Compounds from Canola Oil", *JAOCS*, 65(3):392–395, 1988.

Description of variety for "Regent" (Offical legal document used for variety registration in Canada)., 1988.

Shahidi et al., "Individual Glucosinolates in Six Canola Varieties", *J. Food Quality*, 11:421–431, 1989.

Plant Certificate No. 9100138, 'IMC 01' dated Mar. 31, 1993 of E.I. DuPont de Nemours & Co.

Plant Certificate No. 9000149, 'Cathy' dated Jul. 31, 1991 of the University of Idaho.

Plant Certificate No. 8500115, 'Topas' dated Apr. 30, 1987 of A.B. Svalof of Sweden.

Daun et al., "Glucosinolates in Seeds and Residues", Analysis of Oilseeds, Fats and Fatty Foods, Elsevier Applied Science, Edited by J.B. Rossell and J.L.R. Pritchard, pp. 185–225, 1991.

Gailliard, 4:58–116, The Biochemistry of Plants, Stumph, ed. Academic Press, NY, 1980.

Hawrysh, "Stability of Canola Oil", Chap. 7, pp. 99–122, Camola and Rapeseed: Production, Chemistry, Nutrition, and Processing Technology, Shahidi, ed., Van Nostrand Reinhold, NY, 1990.

Mensink et al., *New England J. Medicine*, N323, 439–445, 1990.

Scarth et al., *Can. J. Pl. Sci.*, 68, 509–511, 1988.

Mahler et al., 1988, Fatty Acid Composition of Idaho Misc. Ser. No. 125.

Rakow et al., *J. Am. Oil Chem. Soc.*, 50, 400–403, 1973.

Rakow, *Z. Pflanzenzuchtg*, 69, 62–82, 1973.

Brunklaus–Jung et al., *Pl. Breed*, 98, 9–16, 1987.

Report of 1990 Canola/Rapeseed Strain Tests A, Western Canada Canola Rapeseed.

Roy et al., *Plant Breed*, 98, 89–96, 1987.

Paul et al., *Theor. Appl. Genet.*, 72, 706, 709, 1986.

Stefansson et al., *Can. J. Plant Sci.*, 55, 343–344, 1975.

Classen, Oral Presentation, GCIRC Eighth International Rapeseed Congress, Saskatoon, Saskatchewan, Jul. 9–11, 1991.

Prevot et al., *J. Am. Oil Chem. Soc.*, 67, 161–164, 1990.

Eskin et al., *J. Am. Oil Chem. Soc.*, 68, 1081–1084, 1989.

Mounts, *J. Am. Oil Chem. Soc.* 56, 659–663, 1979.

Hoffmann et al., *Theor. Appl. Genet.*, 61, 225–232, 1982.

Evans et al., *J. Am. Oil Chem. Soc.*, 48, 711–714, 1970.

Koseoglu et al., Chap. 8, pp. 123–148, In: F. Shahidi ed. Canola and Rapeseed: Production, Chemistry, Nutrition and Processing Technology, Van Nostrand Reinhold, NY 1990.

Pleines et al., Proceedings of the 7th International Rapeseed Congress, p. 23, 1987.

Robbelen et al., *Z. Pflanzenzuchtg.*, 75, 93–105, 1975.

Ram et al., Proceedings of the World Conference on Biotechnology for the Fats and Oils Industry, pp. 65–71, Thomas H. Applewhite, Ed., 1987.

Pleines et al., *Fat. Sci. Technol.*, 89(11), 1987.

Robbelen et al, Proceedings of the International Conference of the Science, Technology fo Rapeseed and Rapeseed Products, 1987.

Downey et al., *Can. J. Plant Sci.*, 43, 271–275, 1963.

Neidleman, Temperature Effects in the Biosynthesis of Unique Fats and Fatty Acids., 1983.

Tremolierres et al., *Phytochemistry*, 21(1), 41–45, 1982.

Craig, *Can. J. Plant Science*, 41, 204–210, 1961.

Rennie et al., *JAOCS*, 66(11), 1622–1624, 1989.

Ullrich et al., *JAOCS*, 65(8), 1313–1317, 1988.

Mounts, Chap. 15, Evaluation of Finished Oil Quality., 1985.

Western Canada Canola Rapeseed Recommendations Committee 1990 Cooperative Trial Data., 1985.

Roy et al., *Z. Pflanzenzuchtung*, 95, 201–209, 1985.

* cited by examiner

*Fig.2* Oxidative Stability by Accelerated Aging para-Anisidine Value IMC 01 vs Alto Flavor Stability by Accelerated Aging
Off-Flavor Intensity IMC 01 vs Alto Overall Acceptance Score vs Off-Flavor Intensity
IMC and Alto Flavor Stability Test
R-squared = -0.9485

Oxidative Stability by Accelerated Aging
Peroxide Value IMC 02 vs Stellar

Oxidative Stability by Accelerated Aging
para-Anisidine Value IMC O2 vs Stellar

Flavor Stability by Accelerated Aging
Overall Acceptance IMC O2 vs Stellar

Flavor Stability by Accelerated Aging
Off-Flavor Intensity IMC O2 vs Stellar

Overall Acceptance Scores vs Off-Flavor Intensity
IMC 02 vs Stellar Flavor Stability Test
R-squared = -0.9428

CANOLA VARIETY PRODUCING A SEED WITH REDUCED GLUCOSINOLATES AND LINOLENIC ACID YIELDING AN OIL WITH LOW SULFUR, IMPROVED SENSORY CHARACTERISTICS AND INCREASED OXIDATIVE STABILITY

This is a divisional of application Ser. No. 08/290,660 now U.S. Pat. No. 5,750,807, filed Aug. 15, 1994, which is a continuation-in-part of application Ser. No. 08/140,205, filed Nov. 12, 1993, now abandoned, which claims priority to PCT/US92/08140, filed Sep. 30, 1992, which is a continuation of application Ser. No. 07/767,748, filed Sep. 30, 1991, now abandoned.

TECHNICAL FIELD

This invention relates to improved canola seeds, plants and oil having advantageous properties, that is, a low glucosinolates content and a very low α-linolenic acid ($C_{18:3}$) content, which produce an oil with low sulfur content, improved sensory characteristics and oxidative stability.

BACKGROUND

A need exists for an improved vegetable oil with a significantly extended shelf life and greater heat stability relative to generic canola oil and a positive nutritional contribution to animal, including human, diets.

Canola oil has the lowest level of saturated fatty acids of all vegetable oils. "Canola" refers to rapeseed (Brassica) which has an erucic acid ($C_{22:1}$) content of at most 2 percent by weight based on the total fatty acid content of a seed, preferably at most 0.5 percent by weight and most preferably essentially 0 percent by weight and which produces, after crushing, an air-dried meal containing less than 30 micromoles (μmol) per gram of defatted (oil-free) meal. These types of rapeseed are distinguished by their edibility in comparison to more traditional varieties of the species.

As consumers become more aware of the health impact of lipid nutrition, consumption of canola oil in the U.S. has increased. However, generic canola oil cannot be used in deep frying operations, an important segment of the food processing industry.

Canola oil extracted from natural and previously commercially useful varieties of rapeseed contains a relatively high (8–10%) α-linolenic acid content ($C_{18:3}$) (ALA). This trienoic fatty acid is unstable and easily oxidized during cooking, which in turn creates off-flavors of the oil (Gailliard, 1980, Vol. 4, pp. 85–116 In: Stumpf, P. K., ed., The Biochemistry of Plants, Academic Press, New York). It also develops off odors and rancid flavors during storage (Hawrysh, 1990, Stability of canola oil, Chapter 7, pp. 99–122 In: F. Shahidi, ed. Canola and Rapeseed: Production, Chemistry, Nutrition, and Processing Technology, Van Nostrand Reinhold, New York). One such unsatisfactory species heretofore has been Brassica napus, i.e., spring canola, a type of rapeseed.

It is known that reducing the α-linolenic content level by hydrogenation increases the oxidative stability of the oil. Hydrogenation is routinely used to reduce the polyunsaturates content of vegetable oils, thereby increasing its oxidative stability. The food industry has used hydrogenation to raise the melting point of vegetable oils, producing oil-based products with textures similar to butter, lard and tallow. Trans isomers of unsaturated fatty acids are commonly produced during hydrogenation. However, the nutritional properties of trans fatty acids mimic saturated fatty acids, thereby reducing the overall desirability of hydrogenated oils (Mensink et al., *New England J. Medicine* N323:439–445, 1990; Scarth, et al., *Can. J. Pl. Sci.*, 68:509–511, 1988). Canola oil produced from seeds having a reduced α-linolenic acid content would be expected to have improved functionality for cooking purposes with improved nutritional value, and therefore have improved value as an industrial frying oil.

However, in general, very little variation exists for α-linolenic acid content in previously known canola quality *B. napus* germplasm (Mahler et al., 1988, Fatty acid composition of Idao Misc. Ser. No. 125). Lines with levels of α-linolenic acid lower than that of generic canola oil are known, but have sensory, genetic stability, agronomic or other nutritional deficiencies. For example, Rakow et al. (*J. Am. Oil Chem. Soc.*, 50:400–403, 1973), and Rakow (Z. Pflanzenzuchtg, 69:62–82, 1973), disclose two α-linolenic acid mutants, M57 and M364, produced by treating rapeseed with X-ray or ethylmethane sulfonate. M57 had reduced α-linolenic acid while M364 had increased α-linolenic acid. However, the instability of the fatty acid traits between generations was unacceptable for commercial purposes.

Brunklaus-Jung et al. (*Pl. Breed.*, 98:9–16, 1987), backcrossed M57 and other rapeseed mutants obtained by mutagenic treatment to commercial varieties. $BC_0$ and $BC_1$ of M57 contained 29.4–33.3% of linoleic acid ($C_{18:2}$) and 4.9–10.8% of α-linolenic acid ($C_{18:3}$). The oleic acid ($C_{18:1}$) content was not reported, but by extrapolation could not have exceeded 60%.

Four other lower α-linolenic acid canola lines have been described. Stellar, reported by Scarth et al. (*Can. J. Plant Sci.*, 68:509–511, 1988), is a Canadian cultivar with lower α-linolenic acid (also 3%) derived from M57. Its α-linolenic acid trait was generated by seed mutagenesis. S85-1426, a Stellar derivative with improved agronomic characteristics, also has lower (1.4%) α-linolenic acid (Report of 1990 Canola/Rapeseed Strain Test A, Western Canada Canola Rapeseed Recommending Committee). IXLIN, another lower α-linolenic acid (1.8%) line described by Roy et al. (*Plant Breed.*, 98:89–96, 1987), originated from an interspecific selection. EP-A 323 753 (Allelix) discloses rape plants, seeds, and oil with reduced α-linolenic acid content linked to limitations in the content of oleic acid, erucic acid, and glucosinolate.

Another nutritional aspect of rapeseed, from which canola was derived, is its high (30–55 μmol/g) level of glucosinolates, a sulfur-based compound. When the foliage or seed is crushed, isothiocyanate esters are produced by the action of myrosinase on glucosinolates. These products inhibit synthesis of thyroxine by the thyroid and have other anti-metabolic effects (Paul et al., *Theor. Appl. Genet.* 72:706–709, 1986). Brassica varieties with reduced glucosinolates content (<30 μmol/g defatted meal) were developed to increase the nutritional value of canola meal (Stefansson et al., *Can. J. Plant Sci.* 55:343–344, 1975). Meal from an ultra-low glucosinolates line, BC86-18, has 2 μmol/g total glucosinolates and significantly improved nutritional quality compared to generic canola meal (Classen, Oral presentation, GCIRC Eighth International Rapeseed Congress, Saskatoon, Saskatchewan, Jul. 9–11, 1991). Neither its fatty acid composition nor its seed glucosinolates profile is known.

There remains a need for an improved canola seed and oil with very low α-linolenic levels in the oil and low glucosinolates in the seed to significantly reduce the need for hydrogenation. The α-linolenic content of such a desirable oil would impart increased oxidative stability, thereby reducing the requirement for hydrogenation and the production of trans fatty acids. The reduction of seed glucosinolates would significantly reduce residual sulfur content in the oil. Sulfur poisons the nickel catalyst commonly used for hydrogenation (Koseoglu et al., Chapter 8, pp. 123–148, In: F. Shahidi, ed. Canola and Rapeseed: Production, Chemistry, Nutrition, and Processing Technology, Van Nostrand Reinhold, New York, 1990). Additionally, oil from a canola variety with low seed glucosinolates would be less expensive to hydrogenate.

SUMMARY OF THE INVENTION

This invention comprises a *Brassica napus* canola yielding seed having a total glucosinolates content of about 18 μmol/g or less of defatted, air-dried meal; the seed yielding extractable oil having 1) an α-linolenic acid content of about 7% or less relative to total fatty acid content of the seed, and 2) a very low sulfur content of less than or equal to 3.00 ppm. The invention also includes a *Brassica napus* yielding canola oil having, when hydrogenated, a significantly reduced overall room-odor intensity relative to the overall room-odor intensity of generic canola oil. The new variety more particularly yields non-hydrogenated oil significantly reduced in fishy odor relative to the fishy odor of generic canola oil, such odor being characteristic of Brassica seed oil. The seed of such canola variety has an α-linolenic acid content of less than or equal to 7%, more preferably less than or equal to about 4.1% α-linolenic acid ($C_{18:3}$) relative to total fatty acid content of said seed and a total glucosinolates content of less than 18 μmol/g, more preferably less than or equal to about 15 μmol/g and most preferably less than or equal to 13 μmol/g and belongs to a line in which these traits have been stable for both the generation to which the seed belongs and that of its parent.

This invention further includes processes of making crosses using IMC 01 as at least one parent of the progeny of the above-described seeds and oil derived from said seeds.

This invention further comprises a seed designated IMC 01 deposited with the American Type Culture Collection, 12301 Parklawn Drive, Rockville, Md., USA 20852 and bearing accession number ATCC 40579, the progeny of such seed and oil of such a seed possessing the quality traits of interest.

DETAILED DESCRIPTION OF THE INVENTION

Figure 1:
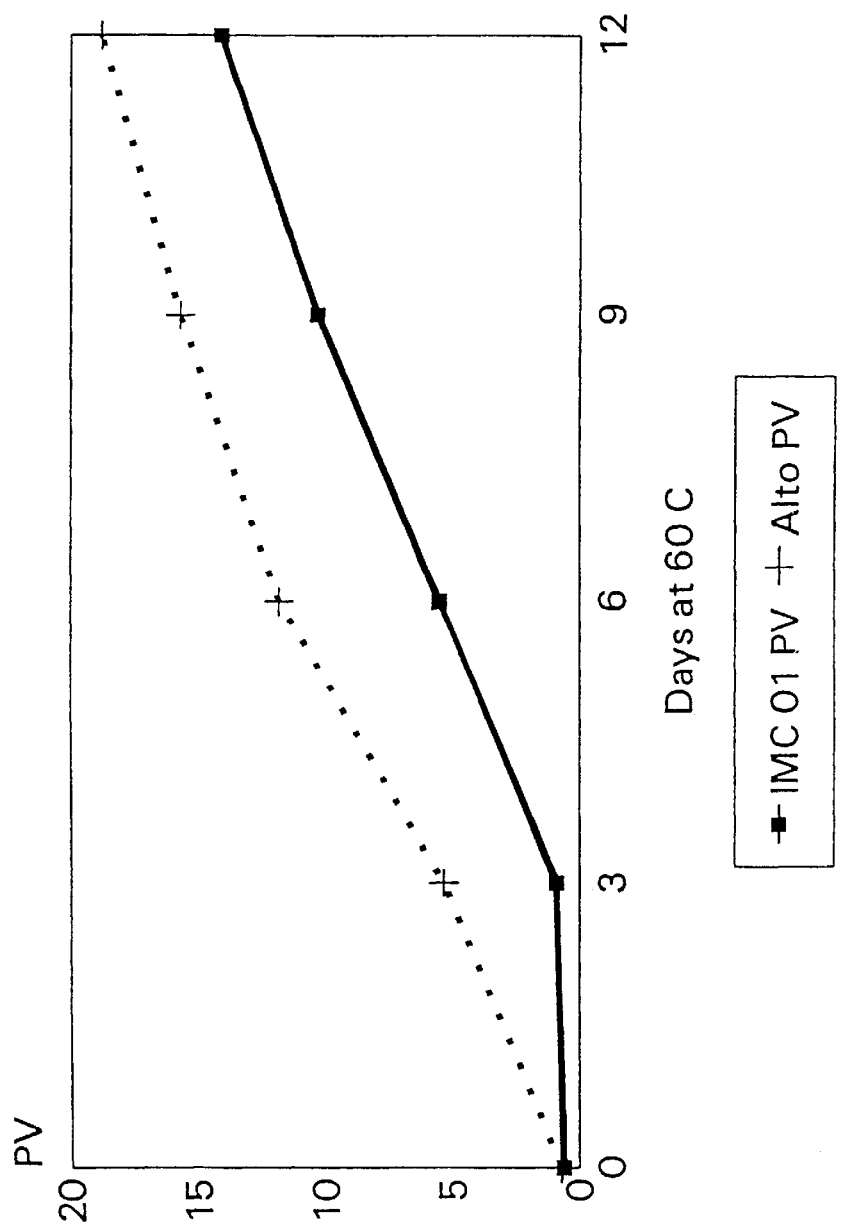
FIG. 1 shows the peroxide values from accelerating aging tests of lines IMC 01 and Alto.

A spring canola (*Brassica napus* L.) variety was developed with improved sensory characteristics and oxidative stability in the seed oil. This variety, designated IMC 01, has very low levels of α-linolenic acid ($CH_3CH_2CH$=$CHCH_2CH$=$CHCH_2CH$=$CH(CH_2)_7COOH$) in the seed oil and very low levels of glucosinolates in the seed. The oil produced from the seed of this variety has very low levels of sulfur and was shown to have significantly improved sensory characteristics over generic canola oils. The IMC 01 is a line in which these traits have been stabilized for both the generation to which the seed belongs and that of its parent generation. Particularly desirable lines of this invention from an agronomic point of view can be derived by conventionally crossing lines producing seeds meeting the definitions of this invention with agronomically well-proven lines such as Westar.

In the context of this disclosure, a number of terms are used. As used herein, a "line" is a group of plants that display little or no genetic variation between individuals for at least one trait. Such lines may be created by several generations of self-pollination and selection, or vegetative propagation from a single parent using tissue or cell culture techniques. As used herein, the terms "cultivar" and "variety" are synonymous and refer to a line which is used for commercial production. "Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner. "Commercial Utility" is defined as having good plant vigor and high fertility, such that the crop can be produced by farmers using conventional farming equipment, and the oil with the described components can be extracted from the seed using conventional crushing and extraction equipment. To be commercially useful, the yield, as measured by both seed weight, oil content, and total oil produced per acre, is within 15% of the average yield of an otherwise comparable commercial canola variety without the premium value traists grown in the same region. "Agronomically elite" means that a line has desirable agronomic characteristics such as yield, maturity, disease resistance, standability. The amount of fatty acids, such as oleic and linolenic acids, that are characteristic of the oil is expressed as a percentage of the total fatty acid content of the oil. "Saturated fatty acid" refers to the combined content of palmitic acid and stearic acid. "Polyunsaturated fatty acid" refers to the combined content of linoleic and α-linolenic acids. The term "shortening" refers to an oil that is a solid at room temperature. The term "room odor" refers to the characteristic odor of heated oil as determined using the room-odor evaluation method described in Mounts (*J. Am. Oil Chem. Soc.*, 56:659–663, 1979). "Generic canola oil" refers to a composite oil extracted from commercial varieties of rapeseed currently known as of the priority date of this application, which varieties generally exhibited at a minimum 8–10% α-linolenic acid content, a maximum of 2% erucic acid and a maximum of 30 µmol/g total glucosinolate level. The seed from each growing region is graded and blended at the grain elevators to produce an acceptably uniform product. The blended seed is then crushed and refined, the resulting oil being sold for use. Table A shows the distribution of canola varieties seeded as percentage of all canola seeded in Western Canada in 1990.

TABLE A

Distribution of Canola Varieties Grown in Western Canada in 1990

| Canola Variety | Percent of Seeded Area |
|---|---|
| *B. campestris* | |
| Candle | 0.4 |
| Colt | 4.4 |
| Horizon | 8.5 |
| Parkland | 2.5 |
| Tobin | 27.1 |
| *B. napus* | |
| Alto | 1.1 |
| Delta | 0.9 |
| Global | 0.9 |
| Legend | 18.2 |
| Pivot | 0.1 |
| Regent | 0.5 |
| Stellar | 0.2 |
| Tribute | 0.4 |
| Triton | 0.7 |
| Triumph | 0.2 |
| Westar | 29.5 |
| Others | 4.4 |

Source: Quality of Western Canadian Canola—1990 Crop Year. Bull. 187, DeClereg et al., Grain Research Laboratory, Canadian Grain Commission, 1404-303 Main Street, Winnipeg, Manitoba, R3C 3G8.

IMC 01 is a very low α-linolenic acid (<4.1% $C_{18:3}$) line selected during an extensive germplasm screening effort. Its parentage is unknown. IMC 01 was self-pollinated and selected for low α-linolenic acid (<4.1%) over four consecutive generations. At each generation, seeds from individually pollinated plants were analyzed for fatty acid composition. Data showed no genetic segregation for α-linolenic acid content over five generations of self-pollinations (Table I). Breeder seed was derived from a bulk seed increase of selected plants from the fourth self-crossed generation.

TABLE I

Fatty Acid Composition of IMC 01 Over Five Generations

| DATE OF ANALYSIS | PERCENT COMPOSITION | | | | |
|---|---|---|---|---|---|
| | $C_{16:0}$ | $C_{18:0}$ | $C_{18:1}$ | $C_{18:2}$ | $C_{18:3}$ |
| 11/87 | 4.1 | 1.9 | 64.1 | 25.7 | 1.9 |
| 8/88 | 4.6 | 2.3 | 72.6 | 14.4 | 2.0 |
| 1/89 | 4.9 | 1.5 | 60.4 | 25.8 | 2.5 |
| 4/89 | 4.8 | 1.8 | 64.3 | 21.4 | 4.0 |
| 10/89 | 4.3 | 2.1 | 64.1 | 24.8 | 2.0 |

IMC 01 was planted in replicated field trials in North Dakota, South Dakota, Minnesota, Washington, Idaho and Montana in 1989 and 1990, under both irrigated and non-irrigated conditions. These tests showed that the α-linolenic acid content of IMC 01 was sensitive to temperature (Table II). This was further supported by growing IMC 01 under controlled temperature conditions in growth chambers. Whether or not the observed temperature sensitivity of IMC 01 is common to other low α-linolenic acid canola lines is unknown.

A temperature effect on fatty acid compositions has been widely reported in plants, especially oilseed crops (Rennie et al., *J. Am. Oil Chem. Soc.*, 66:1622–1624, 1989). These reports describe general temperature effects on fatty acid composition.

Changes in fatty acid content in seed oil under cool temperatures have been documented in plants such as soybean, peanut and sunflower (Neidleman, In: Proceedings of the World Conference on Biotechnology for the Fats and Oils Industry, Applewhite, T. H., ed., pp. 180–183. Am. Oil. Chem. Soc. 1987).

TABLE II

α-Linolenic acid Content of IMC 01 in Production in 1990

| PRODUCTION REGION | $\bar{X}$ TEMPERATURE DURING SEED MATURATION | α-LINOLENIC ACID CONTENT |
|---|---|---|
| Eastern Washington | 74° F. | 1.9% |
| Eastern Washington | 74° F. | 2.0% |
| Northern Idaho | 70° F. | 3.0% |
| Northern Idaho | 67° F. | 2.9% |
| Eastern Idaho | 62° F. | 3.5% |
| Southern Montana | 66° F. | 4.1% |
| Central Montana | 67° F. | 4.0% |

In addition to very low α-linolenic acid, IMC 01 is also characterized by very low levels of glucosinolates. Glucosinolates are sulfur-based compounds common to all Brassica seeds. Glucosinolates exist in aliphatic or indolyl forms. Aliphatic glucosinolates can be analyzed via gas chromatography (GC) (Daun, Glucosinolate analysis of rapeseed (canola), Method of the Canadian Grain Commission, Grain Research Laboratory, Canadian Grain Commission, Winnipeg, 1981). Indolyl glucosinolates have only recently been analyzed via high performance liquid chromatograph (HPLC). Prior to the adoption of the HPLC method, total glucosinolates were calculated by multiplying the aliphatic glucosinolates by a correction factor. Canola quality in the seed is defined as having <30 µmol/g of glucosinolates in the defatted meal.

IMC 01 and Westar were tested in five locations in southeastern Idaho in 1990. Three of the locations were irrigated (I) and two were dryland (D) conditions. Table IIIa shows the difference in total aliphatic glucosinolate between IMC 01 and Westar grown at these locations. The aliphatic glucosinolate values are reported as µmol/gm of defatted meal.

The aliphatic glucosinolate content of IMC 01 by location was consistently lower and more stable than that of Westar at all locations tested. The average glucosinolate contents of IMC 01 was 4.9 µMol/gm while westar was 13.3 µmol/gm. A Least Significant Difference (LSD) test was used to determine if the two were significantly different at all locations. IMC 01 was found to be significantly different from Westar at a level of P<0.05.

HPLC analysis of IMC 01 vs Westar, the most widely grown spring canola variety in North America, shows that IMC 01 has much lower levels of aliphatic glucosinolates (Table III). No significant differences exist for indolyl glucosinolates. Glucosinolates content is also subject to environment influence, e.g., sulfur fertility and drought stress. However, IMC 01 consistently had the lowest and the most stable aliphatic glucosinolates levels at all locations tested (Table IV). The locations tested differ in altitude, temperature, fertility, irrigation, and other cultural practices. Among the low α-linolenic canola lines for which glucosinates analysis have been performed, IMC 01 has the lowest level of total seed glucosinolates (Table V).

TABLE III

Glucosinolates Profiles of IMC 01 and Westar Varieties

| GLUCOSINOLATES (μmol/g) | IMC 01 | WESTAR |
|---|---|---|
| 3-butenyl | 1.2 | 4.2 |
| 4-pentenyl | 0.1 | 0.2 |
| 2-OH-3-butenyl | 3.1 | 7.0 |
| 2-OH-4-pentenyl | 0.9 | 0.4 |
| Total Aliphatics | 5.3 | 11.8 |
| 4-OH-3-indolylmethyl | 6.2 | 6.1 |
| 3-indolylmethyl | 0.8 | 1.0 |
| 4-methoxyindolyl | 0.1 | tr |
| 1-methoxyindolyl | 0.1 | 0.2 |
| Total Indolyls | 7.2 | 7.3 |
| Total Glucosinolates | 12.5 | 19.1 |

TABLE IV

Aliphatic Glucosinolates of IMC 01 and Westar over Different Environments in Southeastern Idaho

| | ALIPHATIC GLUCOSINOLATES CONTENT (μmol/g) | |
|---|---|---|
| LOCATION* | IMC 01 | WESTAR |
| Newdale - I | 4.7 | 13.0 |
| Soda Springs - D | 6.3 | 9.9 |
| Tetonia - D | 5.0 | 13.5 |
| Tetonia - I | 3.7 | 13.3 |
| Shelley - I | 5.0 | 17.0 |
| Average | 4.9 | 13.3 |
| Standard Deviation | 0.93 | 2.51 |

I = Irrigated, D = Dryland

TABLE V

Glucosinolates Content of Low α-Linolenic acid Canola Varieties and Westar

| GLUCOSINOLATES (μmol/g) | ALIPHATIC | INDOLYL | TOTAL |
|---|---|---|---|
| IMC 01 | 5.3 | 7.2 | 12.5 |
| Stellar | 5.2 | 19.5 | 24.7 |
| S85-1426 | 7.9 | 13.4 | 21.3 |
| Westar | 11.8 | 7.3 | 19.1 |

IMC 01 was produced, using normal production practices for spring canola, in Idaho and North Dakota in 1988, in Idaho, Washington State and Montana in 1989, in Idaho, Washington State, Montana, Oregon, and Wyoming in 1990. When grown in suitable environments, where the average daily temperature (high temperature plus low temperature divided by 2) exceeds 20° C., the oil contains <4.1% α-linolenic acid. As an example, a normal fatty acid profile was produced at Casselton, N.Dak. The crop produced in Ashton, Id., was subject to extremely cool conditions and had higher levels of α-linolenic acid. The crops obtained from the field tests were crushed and processed to produce refined, bleached and deodorized (RBD) canola oil at the Protein, Oil, Starch (POS) Pilot Plant in Saskatoon, Saskatchewan. A method of bleaching canola oil is provided in the AOCS' Recommended Practice Cc 8a-52 (AOCS Methods and Standard Practices, 4th Edition (1989)). A method for the refining of crude oils is provided in the AOCS Practice Cc 9a-52 (AOCS Methods and Standard Practices, 4th Edition (1989)). The oils were tested at the Vegetable Oil Research Laboratory, U.S.D.A./Northern Regional Research Center, for organoleptic and sensory characteristics.

Testing to assure that desirable sensory characteristics are obtained in the *Brassica napus* variety was essential. The evaluation of odors has been conducted in a variety of ways on low α-linolenic acid canola oils. The testing methods are based on the fact that vegetable oils emit characteristic odors upon heating. For example, Prevot et al. (*J. Amer. Oil Chemists Soc.* 67:161–164, 1990) evaluated the odors of a French rapeseed, "Westar", and "low linolenic" canola oils in a test which attempted to reproduce domestic frying conditions. In these evaluations the test oils were used to fry potatoes and the odors were evaluated by a test panel. The odor tests showed that the "low linolenic" (approximately 3%) line had a significantly higher (more acceptable) odor score than the French rapeseed and "Westar" lines, which were very similar to each other. Eskin et al. (*J. Amer. Oil Chemists Soc.* 66:1081–1084, 1989) evaluated the odor from canola oil with a low linolenic acid content, a laboratory deodorized sample, and a commercially deodorized sample by sniffing in the presence of the oil itself. These studies demonstrated that a reduction in the linolenic acid content of canola oil from 8–9% to 1.6% reduced the development of heated odor at frying temperatures. However, the odor of the low linolenic acid oil was still unacceptable when heated in air to a majority of the panelists, suggesting that low linolenic acid alone is not sufficient to guarantee acceptable odor.

Mounts (*J. Am. Oil Chem. Soc.*, 56:659–663, 1979) describe a distinct room-odor evaluation method that is used to reproducibly assess the odor characteristics of a cooking oil upon heating. This is the evaluation method of choice owing to its reproducibility and its approximation of odors emitted upon heating the oil. In this method, the oil is heated in a separate chamber and the odor pumped into the room containing the trained evaluators. As noted elsewhere, where the term "room-odor" is used herein, it refers to this method of Mounts. This method is distinct from earlier described tests where the oil and evaluator are within the same room. Such same room testing is referred to as "uncontrolled bench top odor tests" and is considered less accurate and less reliable than the Mounts' room odor evaluation method.

The room-odor characteristics of cooking oils can be reproducibly characterized by trained test panels in room-odor tests (Mounts, *J. Am. Oil Chem. Soc.* 56:659–663, 1979). A standardized technique for the sensory evaluation of edible vegetable oils is presented in AOCS' Recommended Practice Cg 2-83 for the Flavor Evaluation of Vegetable Oils (Methods and Standard Practices of the AOCS, 4th Edition (1989)). The technique encompasses standard sample preparation and presentation, as well as reference standards and method for scoring oils. When heated, generic canola oil has reduced stability and produces offensive room odors. Refined-Bleached-Deodorized (RBD) canola oil is characterized by a fishy flavor in such tests. This characteristic is commonly ascribed to its high polyunsaturated fatty acid content, particularly α-linolenic acid, relative to other vegetable oils. The individual fragrance notes (odor attributes) of the oils are evaluated by Least Significant Difference Analysis. Notes which differ by greater than 1.0 can be reproducibly measured by a sensory panel. In these tests, IMC 01 oil expressed significantly reduced levels of the offensive odors (Table VI).

TABLE VI

Room Odor Intensity of IMC 01 and Generic Canola Oil

| ODOR ATTRIBUTES | IMC 01 | GENERIC CANOLA OIL |
|---|---|---|
| Overall | 4.6$^a$ | 7.4$^b$ |
| Fried Foods | 1.8 | 3.5 |
| Doughy | 1.0 | 0 |
| Fishy | 0$^a$ | 5.5$^b$ |
| Burnt | 0$^a$ | 0.9$^b$ |
| Acrid | 0$^a$ | 2.3$^b$ |
| Woody/Cardboard | 1.9 | 0 |
| Hydrogenated | 0 | 0 |
| Pastry/Sugary | 0 | 0 |
| Waxy | 0 | 0 |
| Chemical | 0 | 0 |

0 = None; 10 = Strong. Scores with different superscript letters are significantly different (P < 0.05). Least Significant Difference for individual odor notes is 1.0. Differences greater than 1.0 can be reproducibly measured by room-odor analysis.

Due to its relatively low stability, canola oil is often hydrogenated for frying. However, hydrogenation produces a characteristic (hydrogenated) room odor which is unacceptable to food manufacturers. Surprisingly, hydrogenated IMC 01 oil also has reduced levels of the characteristic hydrogenated room odor (Table VII). Table VII shows that the overall room-odor intensity of hydrogenated IMC 01 is significantly less than that of hydrogenated generic oil as indicated by a difference is scores of greater than 1.0 in standardized flavor evaluation trials.

TABLE VII

Room Odor Intensity and Individual Odor Descriptions for Hydrogenated Canola Oils

| ODOR ATTRIBUTE | HYDRO-GENATED, GENERIC CANOLA SHORTENING | HYDROGENATED IMC 01 SHORTENING (2% α-LINOLENIC ACID) | HYDRO-GENATED IMC 01 SHORTENING (6.8% α-LINOLENIC ACID) |
|---|---|---|---|
| Overall Intensity | 6.6$^b$ | 3.8$^a$ | 3.9$^a$ |
| Fried Food | 2.7 | 1.1 | 1.5 |
| Doughy | 1.2 | 0.6 | 0.8 |
| Fishy | 0.6 | 0 | 0 |
| Burnt | 0.5 | 0 | 0 |
| Acrid | 0.8 | 0 | 0 |
| Hydrogenated | 3.2 | 1.8 | 2.3 |
| Waxy | 0.5 | 0.6 | 0. |
| Other | 4.5 rubbery flowery weedy soapy | 2.4 fruity smoky | 2.8 fruity flowery sweet pastry |

0 = None; 10 = Strong. Scores with different superscript letters are significantly different (P < 0.05). Least Significant Difference for individual odor notes is 1.0. Differences greater than 1.0 can be reproducibly measured by room-odor analysis.

IMC 01 produces an oil which has improved sensory characteristics. Such improvements have been predicted for low α-linolenic acid canola oils (Ulrich et al., *J. Am. Oil Chem. Soc.*, 8:1313–1317, 1988). However, the improved sensory characteristics of IMC 01 appears not to be related solely to its low α-linolenic acid content. Surprisingly, IMC 01 canola oils with both high and low levels of α-linolenic acid showed similar degrees of improvement. Sensory tests have shown that IMC 01 oil maintains its improved quality at both 2% and 6.8% α-linolenic acid.

The very low glucosinolates characteristic of IMC 01 seed is believed to contribute to the improved sensory characteristic of IMC 01 oil. Glucosinolates in the seed are converted to sulfur compounds. Most of the sulfur breakdown products remain in the meal, but some inevitably contaminate the oil. Lower levels of glucosinolates in the seed are believed to result in lower sulfur content in the oil, and this is believed to reduce the objectionable odor characteristics of canola oil (Abraham et al., *J. Am. Oil Chem. Soc.*, 65:392–395, 1988). An analysis of the sulfur content of IMC 01 oil and several generic canola oils has been performed. IMC 01 oil has approximately one-third the sulfur content of leading generic canola oils (Table VIII).

TABLE VIII

Sulfur Content of Canola Oils

| Canola Oils | Sulfur Content |
|---|---|
| Acme Brand Canola Oil | 3.8 ppm |
| Hollywood Brand Canola Oil | 3.8 ppm |
| Puritan Brand Canola Oil | 3.9 ppm |
| IMC 01 Canola Oil | 1.3 ppm |

The biochemical, molecular and genetic mechanisms responsible for the room-odor quality of vegetable oils are not fully understood. Improvements in vegetable oil processing technology, i.e., preferential removal of sulfur during processing, less abusive oil extraction procedures, minimal processing, gentler deodorization, etc., may improve the overall quality of vegetable oils, including both sensory and functional characteristics (Daun et al., *J. Am. Oil Chem. Soc.*, 53:169–171, 1976). IMC 01 will benefit from any such processing improvements, and will maintain its improved sensory characteristics over generic canola oil under equivalent processing conditions.

IMC 01 is true breeding as are its progeny. The traits responsible for reduced α-linolenic acid and reduced total glucosinolates in the seed which yield an oil low in sulfur having improved sensory characteristics have a genetic basis. The data presented herein show that these traits are stable under different field conditions. These traits can be removed from the IMC 01 background and are transferred into other backgrounds by traditional crossing and selection techniques.

Crosses have been made with IMC 01 as one parent to demonstrate that the superior IMC 01 quality/sensory traits are transferred along with the superior agronomic traits of another parent such as the Canadian canola line, Westar, into descendants. The parent to which IMC 01 is crossed is chosen on the basis of desirable characteristics such as yield, maturity, disease resistance, and standability. Conventional breeding techniques employed in such crossings are well known by those skilled in the art. Thus, a method of using the IMC 01 *Brassica napus* is to cross it with agronomically elite lines to produce plants yielding seeds having the characteristics listed above.

The general protocol is:
a. cross IMC 01 to a selected parent;
b. produce a "gametic array" using microspores of the $F_1$ plants to produce dihaploid (DH) individuals;
c. field trial $DH_2$ individuals for yield and select from IMC 01 α-linolenic acid and glucosinolate levels; and
d. test selected individuals for oil quality using RBD oil.

Example 3 is a specific example of such work to develop descendents to IMC 01 which retain the desirable quality traits. The data of Example 3 show that the quality traits of IMC 01 are heritable in such crosses.

The present invention is further defined in the following Examples, in which all parts and percentages are by weight and degrees are Celsius, unless otherwise stated. It should be understood that this Example, while indicating preferred embodiments of the invention, is given by way of illustration only. From the above discussion and this Example, one skilled in the art can ascertain the essential characteristics of this invention, and without departing from the spirit and scope thereof, can make various changes and modifications of the invention to adapt it to various usages and conditions.

EXAMPLE 1

IMC 01, originally designated DNAP #336, was grown in a greenhouse in Cinnaminson, N.J., over several seasons to select for a stable, very low α-linolenic line. Day/night temperatures from August through December in the greenhouse averaged 80° F./65° F. with fluctuations of ±5° F., 75° F./65° F. from January through April, and 85° F./65° F. from March through July. The plants were grown in 1-gallon pots under natural day length, except from October through May when the plants received 14 hours of supplemental lighting. Flowering racemes were covered with paper bags to prevent cross-pollination, and gently shaken to induce seed set. Watering was decreased as pods reached maturity.

For field testing, IMC 01 was planted in multi-location trials and production plots in Montana, Idaho and Washington. The trials were planted in a completely randomized block design with four replications. Each block contained eight plots of 6 meters by 8 rows. IMC 01 was also planted in large acreages (>25 acres) according to standard agronomic procedures for spring canola production, with a minimum ½-mile isolation from other *Brassica napus* crops. Depending on location, the fields were planted in April or May, and harvested in August or September. Plantings were made on dryland, following both fallow or recrop, or under irrigation. Mature pod samples were taken following swathing for chemical analysis.

For fatty acid analysis, 10–50 seed samples were ground in 15-mL polypropylene tubes and extracted in 1.2 mL 0.25 N KOH in 1:1 ether/methanol. The sample was vortexed for 10 sec and heated for 60 sec and in 60° C. water bath. Four mL of saturated NaCl and 2.4 mL of iso-octane were added, and the mixture was vortexed again. After phase separation, 600 $\mu$L of the upper organic phase was pipetted into individual vials and stored under nitrogen. One $\mu$L sample was injected into a Supelco SP-2330 fused silica capillary column (0.25 mm ID, 30 m length, 0.20 $\mu$m df, Bellfonte, Pa.).

The gas chromatograph was set at 180° C. for 5.5 min, then programmed for a 2° C./min increase to 212° C., and held at this temperature for 1.5 min. Chromatography settings were: Column head pressure—15 psi, Column flow (He)—0.7 mL/min, Auxiliary and Column flow—33 mL/min, Hydrogen flow=33 mL/min, Air flow—400 mL/min, Injector temperature—250° C., Detector temperature—300° C., Split vent—1/15.

A standard industry procedure for HPLC analysis of glucosinolates was used to analyze the glucosinolates composition of the seed (Daun et al., In: Glucosinolate Analysis of Rapeseed (Canola). Method of the Canadian Grain Commission, Grain Research Laboratory, 1981).

IMC 01 seed was harvested and processed to produce refined, bleached and deodorized (RBD) oil. Some oil was hydrogenated after refining, bleaching and deodorization, then redeodorized.

Before extraction, the seed was tempered to adjust the moisture content to 9% and flaked to 0.38 to 0.64 cm in a ribbon blender. The flakes were cooked in a stack cooker at 82.8° C. for 30 min (8.5% moisture) and pre-pressed with vertical and horizontal bar spacings set to 0.031 cm, vertical shaft speed at 40 rpm and horizontal shaft at 25 rpm. The press cake was extracted in a Crown Model 2 extractor at 37.3 kg and hexane extracted with a 2:1 solvent to solids ratio.

The crude oil was alkali refined at 65° C.–70° C. for 30 min with 0.2% to 85% phosphoric acid, then mixed with sodium hydroxide to neutralize free fatty acids. Soaps were removed with a water wash (65° C. water, 5 min) and the oils bleached with 0.75% each by weight of Clarion and Acticil bleaching earths for 30 min to remove color bodies. The resulting oil contained no peroxides, 0.08% free fatty acids, and had a Gardner color of 10-.

The oil was continuously deodorized at 265° C. at 300 kg/h. The steam rate was 1% of feed rate. The deodorized oil was preheated to 68–72° C. prior to deaeration. RBD oil was stored in food grade plastic drums or pails at 4° C. under nitrogen prior to testing.

For hydrogenation, RBD oil was heated to 350° F. under vacuum in a stainless steel pressure reactor. A 0.5% sulfur-poisoned nickel catalyst, Englehardt SP-7, was added to the oil at 80.1° C., and hydrogen gas was introduced at 40 psi. Periodic samples were analyzed until an oil with a 30.5° C. melting point was achieved. The hydrogenated oil was redeodorized and stored by the methods described previously.

The RBD and hydrogenated oil samples were analyzed for room-odor characteristics by a trained test panel in comparison with a generic, commercially available RBD canola oil (Proctor & Gamble) and generic, commercially available hydrogenated canola shortening as described previously. The testing protocol used is described in Mounts (*J. Am. Oil Chem. Soc.* 56:659–663, 1979) which is hereby incorporated by reference. The testing controlled for temperature of the oil, distance from the oil and room volume, and required that the oil was heated in a separate chamber and pumped into the room containing the trained panelist.

Specifically, room odor profiles of IMC 01 and a generic canola oil were obtained as follows:

A. Room Odor Protocol

A 150 mL sample of the selected oil was heated to 190° C. for 30 min before the start of each panel test. The oil was maintained at this temperature throughout each session. For each session a fresh oil sample was used.

Panelists visited each odor room for approximately 15 sec. A five min rest was required between visits. Visitation to each odor room was randomized among the panelists.

The trained panelists judged the room. Qdor for intensity of odor, quality of odor, and odor attributes. The intensity was ranked as: 0–4 weak, 5–7 moderate, and 8–10 strong. The quality of odor was judged as: 0–1 bad, 2–3 poor, 4–6 fair, 7–8 good, and 9–10 excellent. The odor attributes were ranked as: 0–1 bland, 2–4 weak, 5–7 moderate, and 8–10 strong. The flavor attributes were fried, painty, fishy, hydrogenated, burnt, cardboard, metallic, rubbery, waxy, buttery, and nutty.

B. Generic Oil—IMC 01 Profile Comparison

A generic, commercially available canola oil (Proctor & Gamble) was used in the IMC room odor tests as the standard or generic canola oil. In a comparative test, the standard canola oil was significantly (P<0.05) higher in room odor intensity than IMC 01 (Table IX). The standard canola oil odor was of "moderate" intensity while the IMC 01 was considered "weak". The overall quality of the IMC 01 room odor was significantly (P<0.05) better than the standard canola oil. The standard canola oil had significantly (P<0.05) higher intensities for fried, painty, and cardboard odors than the IMC 01 oil.

TABLE IX

Room Odor Profile of Generic
(Proctor & Gamble) and IMC 01 Oil

| Evaluation* | IMC 01 | Generic |
|---|---|---|
| A. Intensity | 3.4[a] | 5.2[b] |
| B. Quality | 5.8[a] | 4.9[b] |
| C. Odor Attributes | | |
| Fried | 1.9[a] | 2.9[b] |
| Painty | 0.4 | 1.3 |
| Fishy | 0.8[a] | 1.9[b] |
| Hydrogenated | 1.1 | 0.6 |
| Rancid | 0.7 | 0.9 |
| Burnt | 0.8 | 1.4 |
| Cardboard | 0.1[a] | 1.5[b] |
| Metallic | 0.5 | 0.1 |
| Rubbery | 0.0 | 0.0 |
| Waxy | 0.6 | 0.0 |
| Buttery | 0.7 | 0.3 |

*The "intensity" was ranked as: 0–4 weak, 5–7 moderate, and 8–10 strong. The "quality" of odor was judged as: 0–1 bad, 2–3 poor, 4–6 fair, 7–8 good, and 9–10 excellent. The "odor attributes" were ranked as: 0–1 bland, 2–4 weak, 5–7 moderate, and 8–10 strong.
Scores with different superscript letters are significantly different (P < 0.05).

Pilot plant-processed samples of Example 2 generic canola (low erucic acid rapeseed) oil and oil from IMC 01 canola with the fatty acid compositions modified by mutation breeding and/or hydrogenation were evaluated for frying stability α-linolenic acid contents were 10.1% for generic canola oil, 1.7% for canola modified by breeding (IMC 01) and 0.8% and 0.7% for IMC 01 oils modified by breeding and hydrogenation. The IMC 01 modified oils had significantly (P <0.05) less room odor intensity that the generic canola oil after initial heating tests at 190° C. as judged by a sensory panel under conditions of AOCS Cg 2-83. The generic canola oil had significantly higher intensities for fishy, burnt, rubbery, smoky, and acrid odors than the modified oils. Foam heights of the modified oils were significantly (P <0.05) less than those of the generic oil after 20, 30 and 40 hrs of heating and frying at 190° C. The flavor quality of french fried potatoes was significantly (P <0.05) better for all the potatoes fried in modified oils than those fried in generic canola oil. The potatoes fried in generic canola oil were described by the sensory panel as fishy. No off-flavors were detected in potatoes fried in the modified oils.

EXAMPLE 3

This Example demonstrates that the traits of very low α-linolenic acid and very low glucosinolate content are transferred to IMC 01 progeny.

Year 1  IMC 01                X   Westar
        ALA Content: 2.5%         ALA Content: 8.5%
        Glucosinolates: 12 μmol/g  Glucosinolates: 21 μmol/g

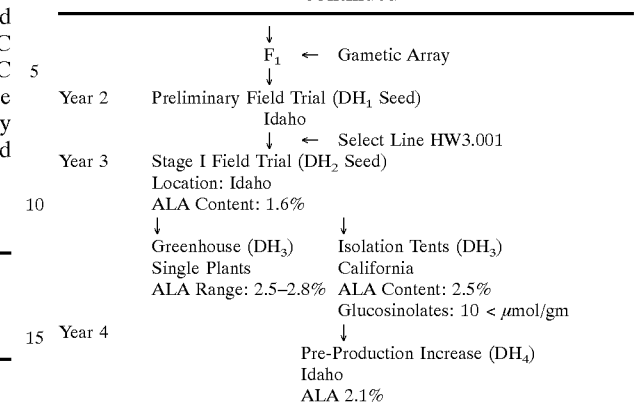

The pre-production will be crushed and the oil refined for quality.

Once a canola line has been stabilized, fully conventional methods of plant biotechnology, breeding and selection are used to further enhance, for example, the agronomic properties of the resultant line in order to improve important factors such as yield, hardiness, etc. Such techniques are also well known and include, e.g., somaclonal variation, seed mutagenesis, anther and microspore culture, protoplast fusion, etc. See, e.g., Brunklaus-Jung et al., *Pl. Breed.*, 98:9–16, 1987; Hoffmann et al., *Theor. Appl. Genet.*, 61, 225–232 (1982), each herein incorporated by reference).

A deposit of seed designated IMC 01 has been made in the American Type Culture Collection (ATCC) depository (Rockville, Md. 20852) and bears accession number ATCC 40579. The deposit was made on Mar. 2, 1989 under conditions complying with the requirements of the Budapest Treaty.

EXAMPLE 4

IMC 01 was compared to Alto, a "generic" variety of commercial canola oil.

Oils were processed using standard commercial refining, bleaching and deodorizing processes.

TABLE X

Processed Oil Analysis

| | IMC 01 | Alto |
|---|---|---|
| Red color | 0.5 | 0.7 |
| Yellow color | 4 | 5 |
| para-anisidine value | 0.97 | 2.32 |
| Peroxide value, meg/g | 0.6 | 0.7 |
| TOTOX value – p-av + 2(pv) | 2.07 | 3.72 |
| Total Polymers, % | 0.02 | 0.01 |
| Total Polar Material, % | 0.77 | 0.36 |
| Free fatty acid, % | 0.022 | 0.013 |
| Fatty acid composition, % | | |
| C16:0 | 4.2 | 4.0 |
| C18:0 | 2.2 | 2.0 |
| C18:1 | 63.5 | 62.5 |
| C18:2 | 22.2 | 18.3 |
| C18:3 | 4.9 | 7.7 |

Results: Chemical analysis indicates oils were processed within industry standards for quality vegetable oils (see Table X). Based on AOCS Recommended Practice Cg 3-91; oils with a TOTOX value of less than 4.0 indicate good stability. TOTOX value=para-anisidine value+2 (peroxide value).

Colors determined by American Oil Chemists' Society (AOCS) method Cc 13b-43, using American Oil Tintometer, Model AF715, The Tintometer LTD., Salisbury, England.

para-Anisidine Value (p-av) determined by AOCS method Cd 18-90, measures secondary oxidation by-producs in oils.

Peroxide Value determined by AOCS method Cd 8b-90, measures the primary oxidation product in oils.

Total polymers determined by AOCS method Cd 22-91, gel-permeation HPLC.

Total Polar Materials determined by AOCS method Cd 20-91, packed column method to HPLC.

Free fatty acid determined by AOCS method Ca 5a-40.

Fatty acid composition determined by AOCS method Ce le-91, capillary gas liquid chromatography.

Oxidative Stability by Oxidative Stability Instrument (OSI)

Oxidative stability measured by Automatic Oxygen Method (AOM) hours determined by American Oil Chemists Society (AOCS) method Cd 12b-92, Fat Stability, Oil Stability Index (OSI), using an Oxidative Stability Instrument, manufactured by Omnion/Archer Daniels Midland, Decatur, Ill.

|  | IMC 01 | Alto |
|---|---|---|
| AOM hours | 26.8 | 17.5 |

Results indicate IMC 01 has greater AOM hours and therefore greater oxidative stability than Alto.

Oxidative Stability and Flavor Stability by Accelerated Agina

The Schaal oven method of accelerated aging is used in the oil industry to measure the oxidative and flavor stability of oil. The Schaal oven method involves examining samples of oil at predetermined intervals held at 60° C. in the dark. One day under Schaal oven conditions is equivalent to one month storage in the dark at ambient temperature.

Oxidative stability is measured by monitoring the increases in peroxides (peroxide value) and secondary oxidative by-products (para-anisidine value) in the oils held at 60° C. for twelve days.

Flavor stability is determined by a trained sensory panel using the same oils tested for oxidative stability.

Sample preparation:

400 g of oil placed in 500 mL amber glass bottles (80 mm wide, 140 mm high, with a 42 mm opening), uncapped, held in 60° C. (range 59 to 61° C.) convection oven (Blue M, manufactured by Blue M Electric) for 3, 6, 9 and 12 days. One bottle of oil per day per type of oil was removed from the oven and analyzed for peroxide value, para-anisidine value and sensory characteristics.

Samples were frozen immediately after removing from the oven. Peroxide value, para-anisidine value and sensory evaluation were made within seven days after samples were frozen.

Oxidative Stability by Accelerated Aging

TABLE XI

Changes in Peroxide Value and para-Anisidine Value

| Days | PV IMC 01 | Alto | p-AV IMC 01 | Alto |
|---|---|---|---|---|
| 0 | .6 | 0.7 | 0.97 | 2.32 |
| 3 | 0.9 | 5.33 | 0.99 | 2.52 |
| 6 | 5.48 | 11.8 | 1.36 | 5.02 |
| 9 | 10.3 | 15.7 | 2.45 | 6.5 |
| 12 | 14.1 | 18.8 | 3.42 | 7.49 |

Figure 2:
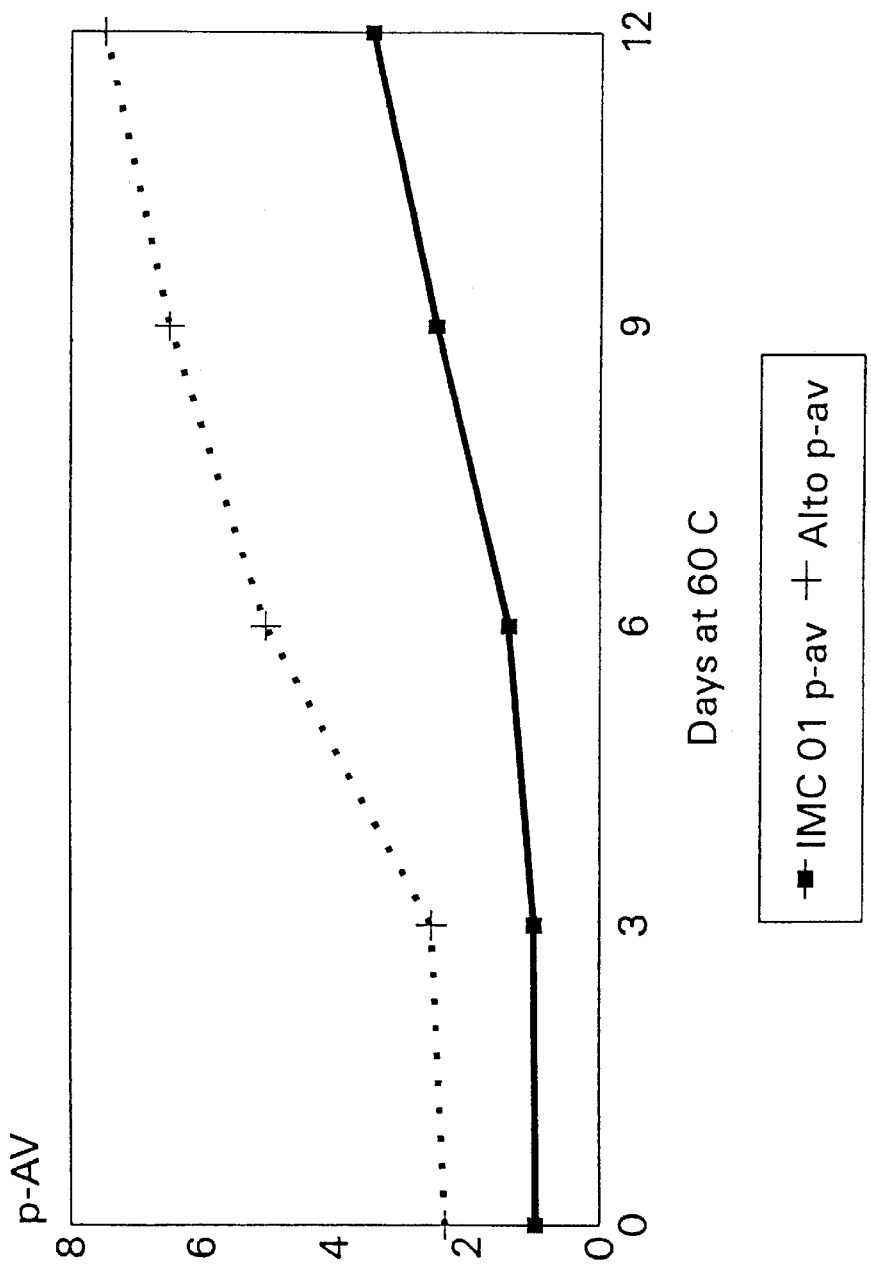
FIG. 2 shows the para-anisidine values from accelerated aging tests of lines IMC 01 and Alto.

(see Figures 1 and 2)

Results: Based on increases in peroxide and p-av values over the 12 day storage period, IMC 01 has greater oxidative stability than Alto (see Table XI).

Flavor Stability by Accelerated Aging:

Sensory panel trained in evaluation of vegetable oils according to protocol of AOCS method Cg 2-83, Flavor Panel Evaluation of Vegetable Oils. Using AOCS flavor standards panel members were trained to identify the following off flavors; fishy, green, cardboard, plastic and painty.

TABLE XII

Overall Acceptance Scores and Total Off-Flavor Intensities

| Day | Overall Acceptance[1] | | Total Off-Flavors[2] | |
|---|---|---|---|---|
|  | IMC 01 | Alto | IMC 01 | Alto |
| 0 | 7.53 | 6.01 | 0.59 | 2.32 |
| 3 | 7.04 | 3.2 | 0.87 | 8.29 |
| 6 | 5.44 | 3.10 | 4.17 | 9.46 |
| 9 | 3.81 | 1.78 | 6.22 | 10.15 |
| 12 | 4.00 | 2.00 | 7.16 | 12.89 |

[1]Overall acceptance scores are based on a 0–9 scale; 0 is extremely unacceptable and 9 is very acceptable.
[2]Total off-flavor intensities include fishy, green, cardboard, and painty. Ratings are based on a 0–15 scale, were 0 is bland and 15 is very intense.

Figure 3:
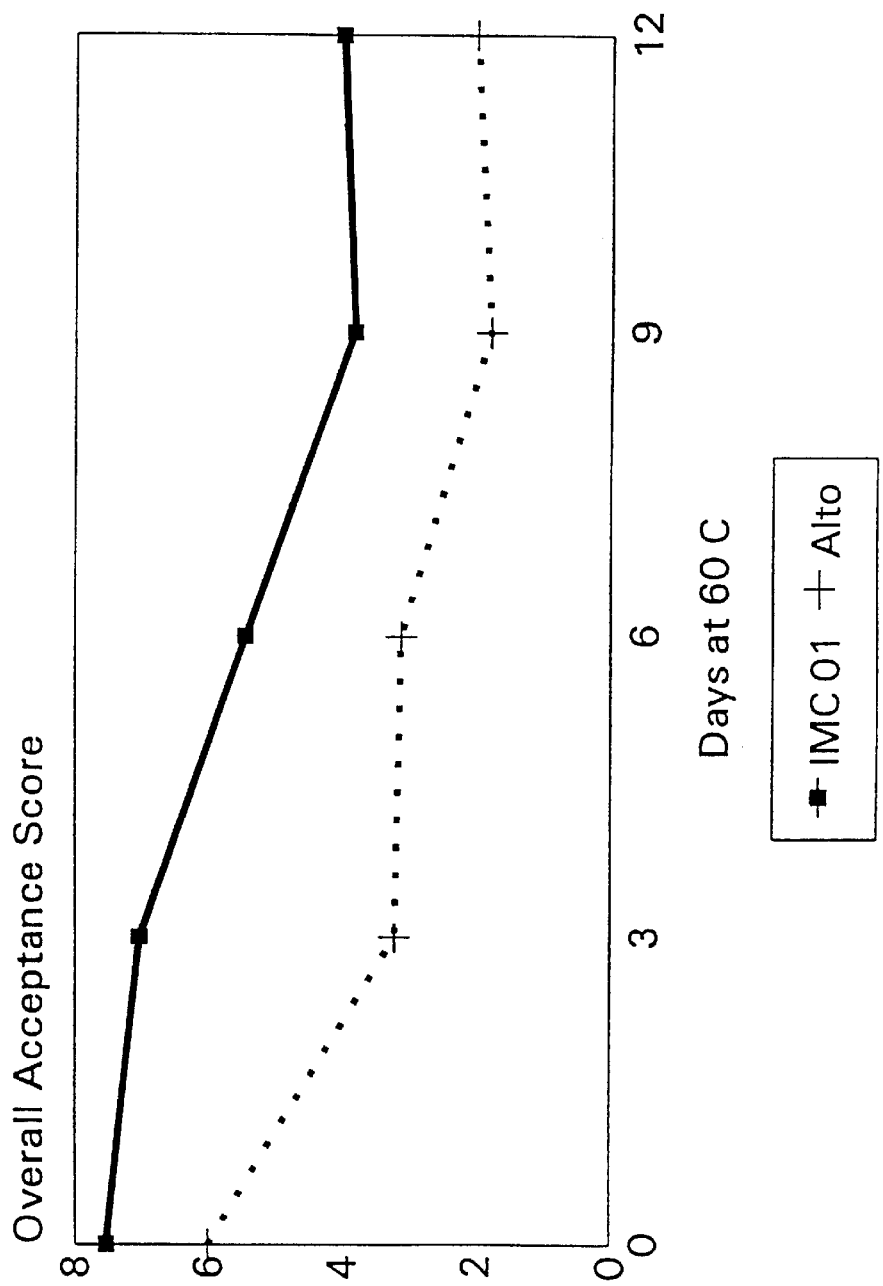
FIG. 3 shows the overall acceptance scores from accelerated aging tests for IMC 01 and Alto.
Figure 4:
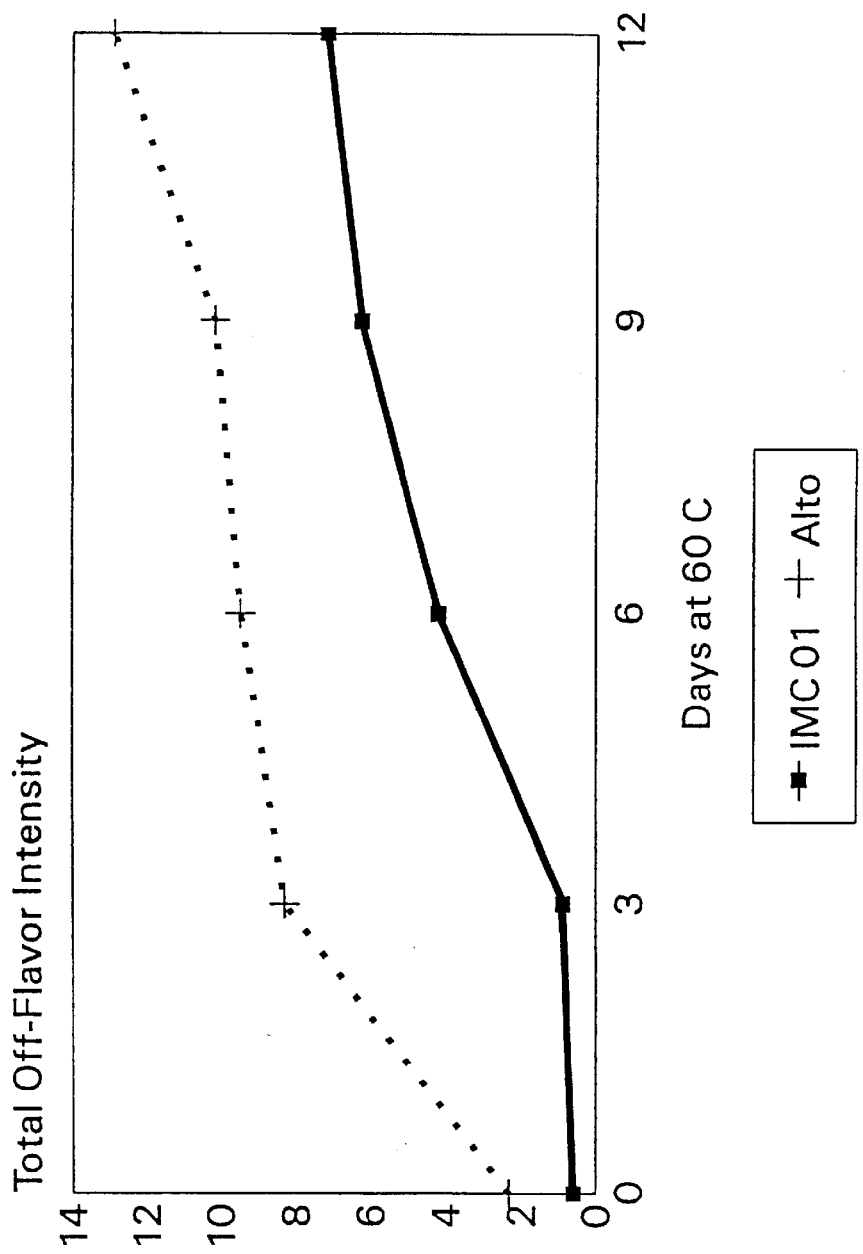
FIG. 4 shows the off-flavor intensity scores from accelerated aging tests for IMC 01 and Alto.

Results:

Overall acceptability scores were significantly different after 0, 3, 6, 9, and 12 days (p=0.05) (see Table XII and FIGS 3 and 4).

Figure 5:
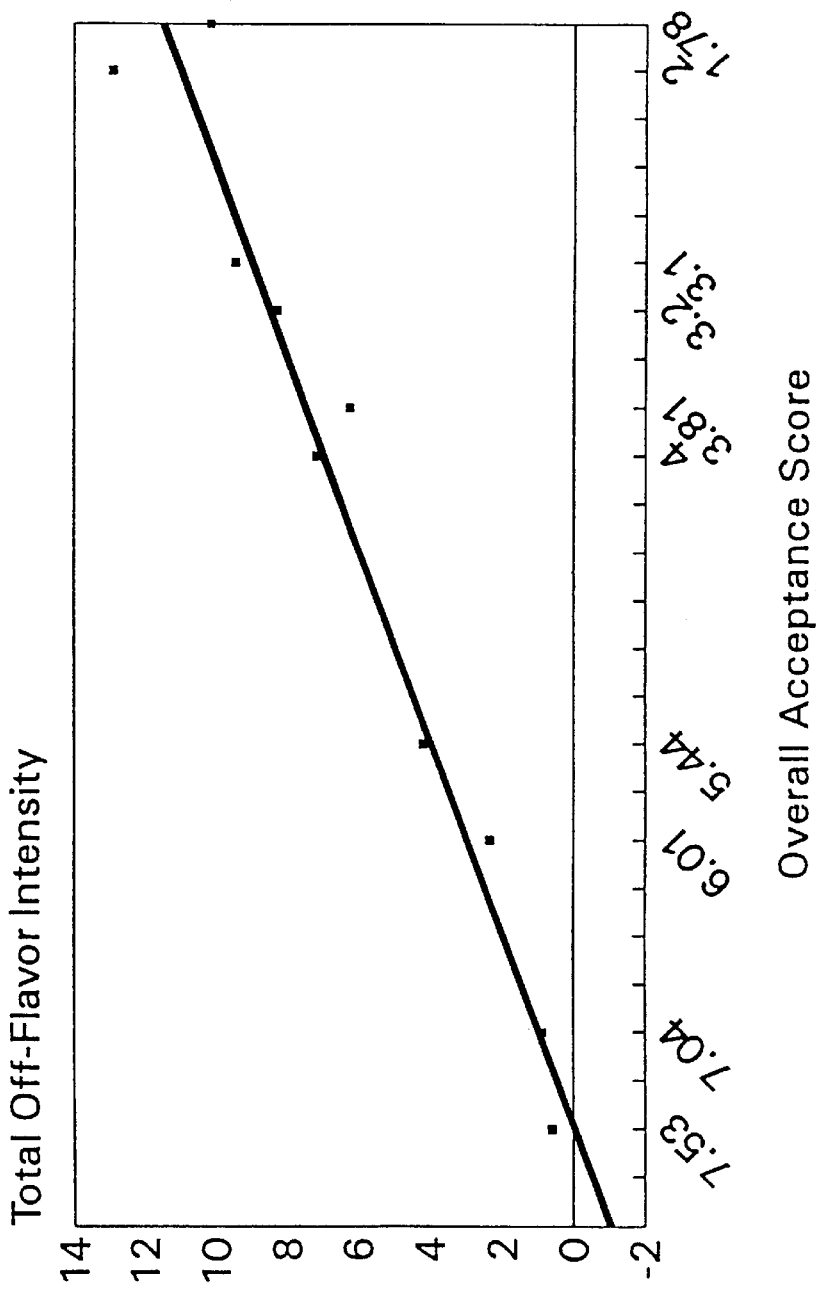
FIG. 5 shows a linear regression analysis of overall acceptance scores versus off-flavor intensity scores for IMC 01 and Alto.

Correlation between overall acceptance score and total off-flavors $r^2$-0.9485 (see FIG. 5).

Significantly lower overall acceptance scores and lower total off-flavor intensities indicates IMC 01 has significantly better flavor stability than Alto.

EXAMPLE 5

IMC 02 was compared to Stellar, a commercially available low alpha linolenic variety of canola.

TABLE XIII

Processed Oil Analysis

|  | IMC 02 | Stellar |
|---|---|---|
| Red color | 0.2 | 0.3 |
| Yellow color | 3 | 3 |
| para-Anisidine value | 0.48 | 0.78 |
| Peroxide value, meq/g | 0.2 | 0.6 |
| TOTOX value = p-av + 2(pv) | 0.88 | 1.98 |
| Total Polymers, % | 0.01 | 0 |
| Total Polar Material, % | 0.63 | 0.42 |

TABLE XIII-continued

Processed Oil Analysis

|  | IMC 02 | Stellar |
|---|---|---|
| Free fatty acid, % | 0.026 | 0.014 |
| Fatty acid composition, % | | |
| C16:0 | 3.8 | 4 |
| C18:0 | 2.2 | 2.3 |
| C18:1 | 66.3 | 62.8 |
| C18:2 | 22.3 | 24.4 |
| C18:3 | 2.7 | 3.3 |

Results: Chemical analysis indicates oils were processed within industry standards for quality vegetable oils (see Table XIII). Based on AOCS Recommended Practice Cg 3-91; oils with a TOTOX value of less than 4.0 indicate good stability. TOTOX value=para-anisidine value+2 (peroxide value).

Oxidative Stability - OSI AOM Hours

|  | IMC 02 | Stellar |
|---|---|---|
| AOM hours | 31.5 | 23.1 |

Results indicate IMC 02 has greater AOM hours and therefore greater oxidative stability than Stellar.

Oxidative Stability by Accelerated Aging

TABLE XIV

Changes in Peroxide Value and para-Anisidine Value

|  | PV | | p-AV | |
|---|---|---|---|---|
| Days | IMC 02 | Stellar | IMC 02 | Stellar |
| 0 | 0.2 | 0.6 | 0.48 | 0.78 |
| 3 | 0.7 | 1.39 | 0.76 | 0.84 |
| 6 | 1.5 | 3.77 | 0.26 | 0.99 |
| 9 | 4.4 | 7.37 | 0.82 | 2.07 |
| 12 | 9.6 | 13.3 | 1.18 | 2.56 |

Figure 6:
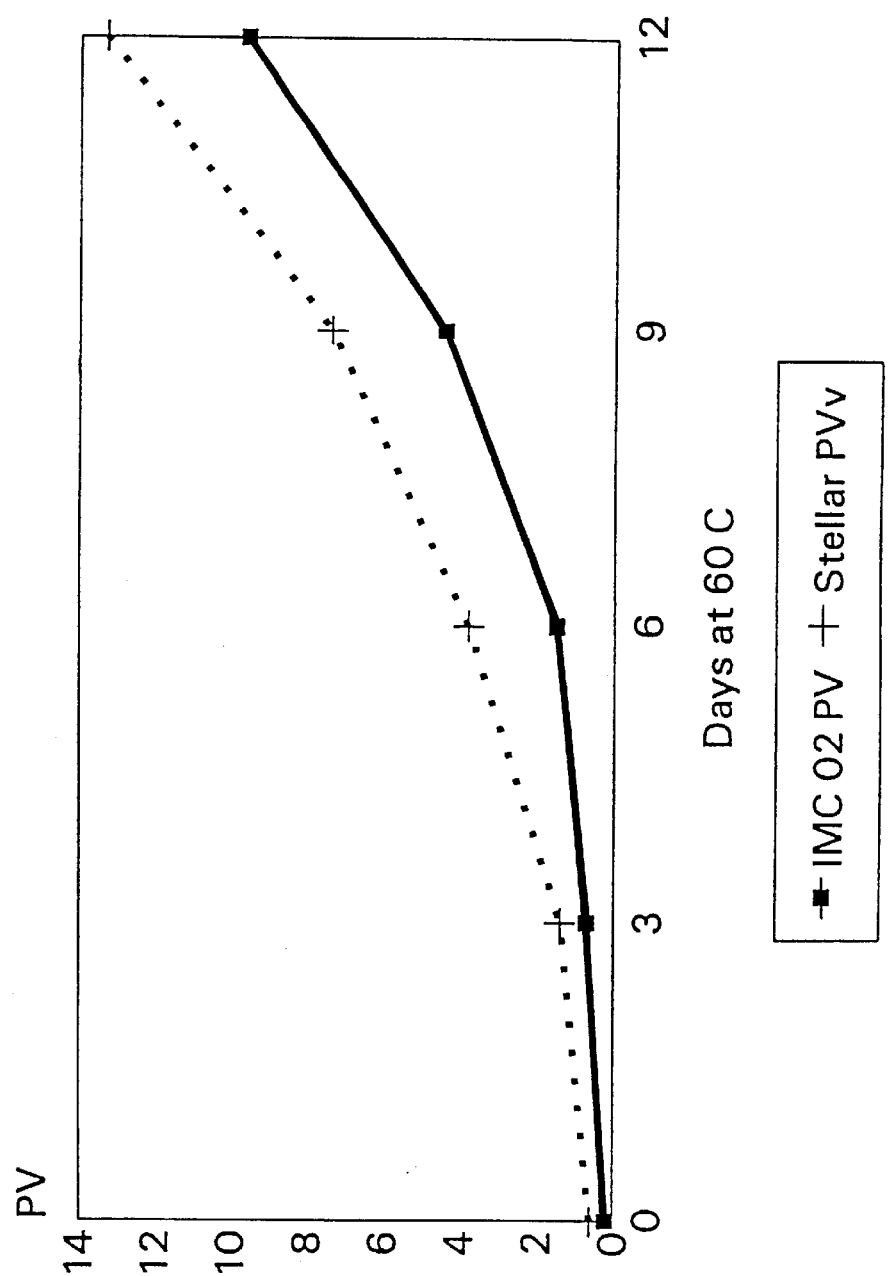
FIG. 6 shows the peroxide values from accelerated aging tests for IMC 02 and Stellar.
Figure 7:
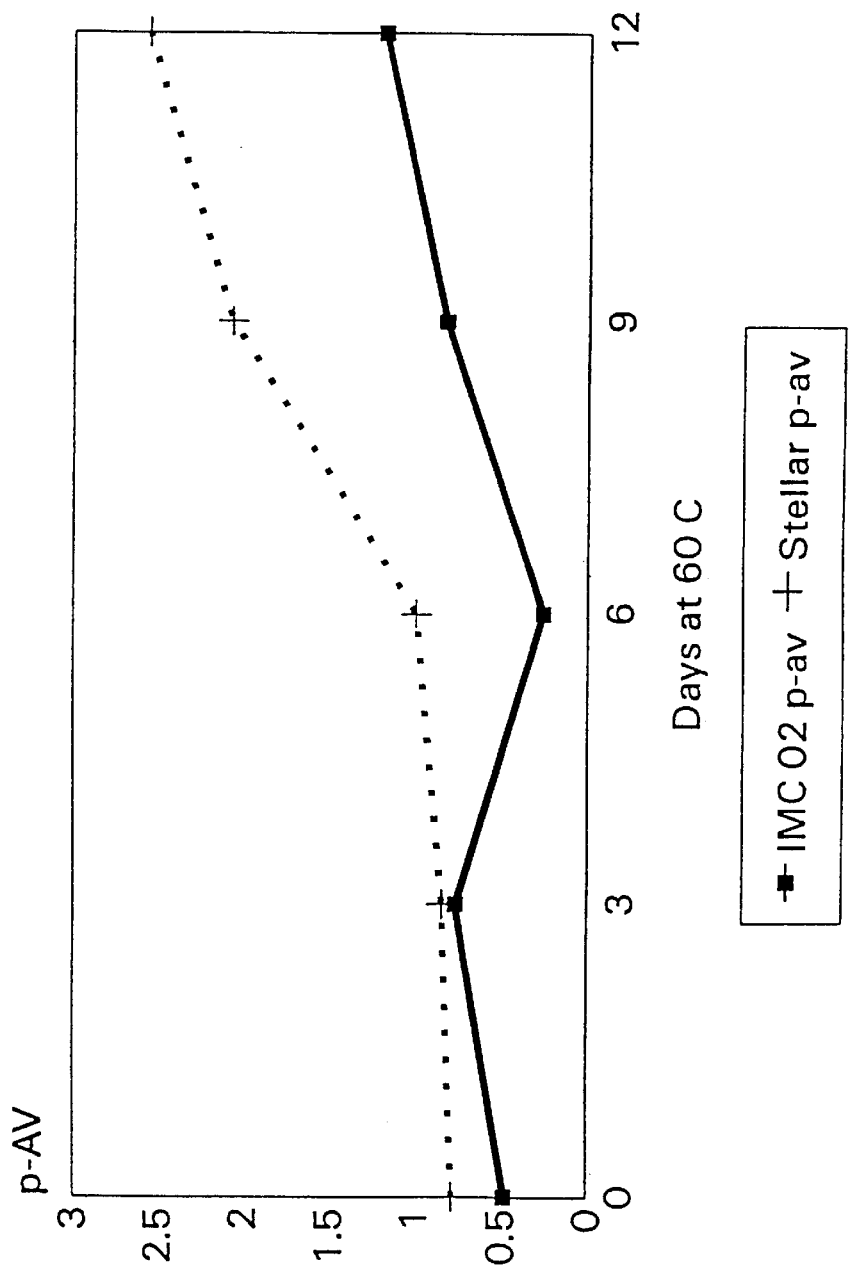
FIG. 7 shows the para-anisidine values from accelerated aging tests for IMC 02 and Stellar.

(See FIGS. 6 and 7)

Results: Based on increases in peroxide and p-av values over the 12 day storage period, IMC 02 has greater oxidative stability than Stellar (see Table XIV).

TABLE XV

Overall Acceptance Scores and Total Off-Flavor Intensities

|  | Overall Acceptance[1] | | Total Off-Flavors[2] | |
|---|---|---|---|---|
| Day | IMC 02 | Stellar | IMC 02 | Stellar |
| 0 | 8.66 | 7.75 | 0.66 | 0.73 |
| 3 | 6.87 | 4.18 | 1.98 | 7.16 |
| 6 | 7.01 | 4.57 | 1.44 | 6.07 |
| 9 | 6.10 | 3.67 | 2.79 | 8.41 |
| 12 | 4.16 | 3.67 | 5.73 | 7.83 |

Figure 8:
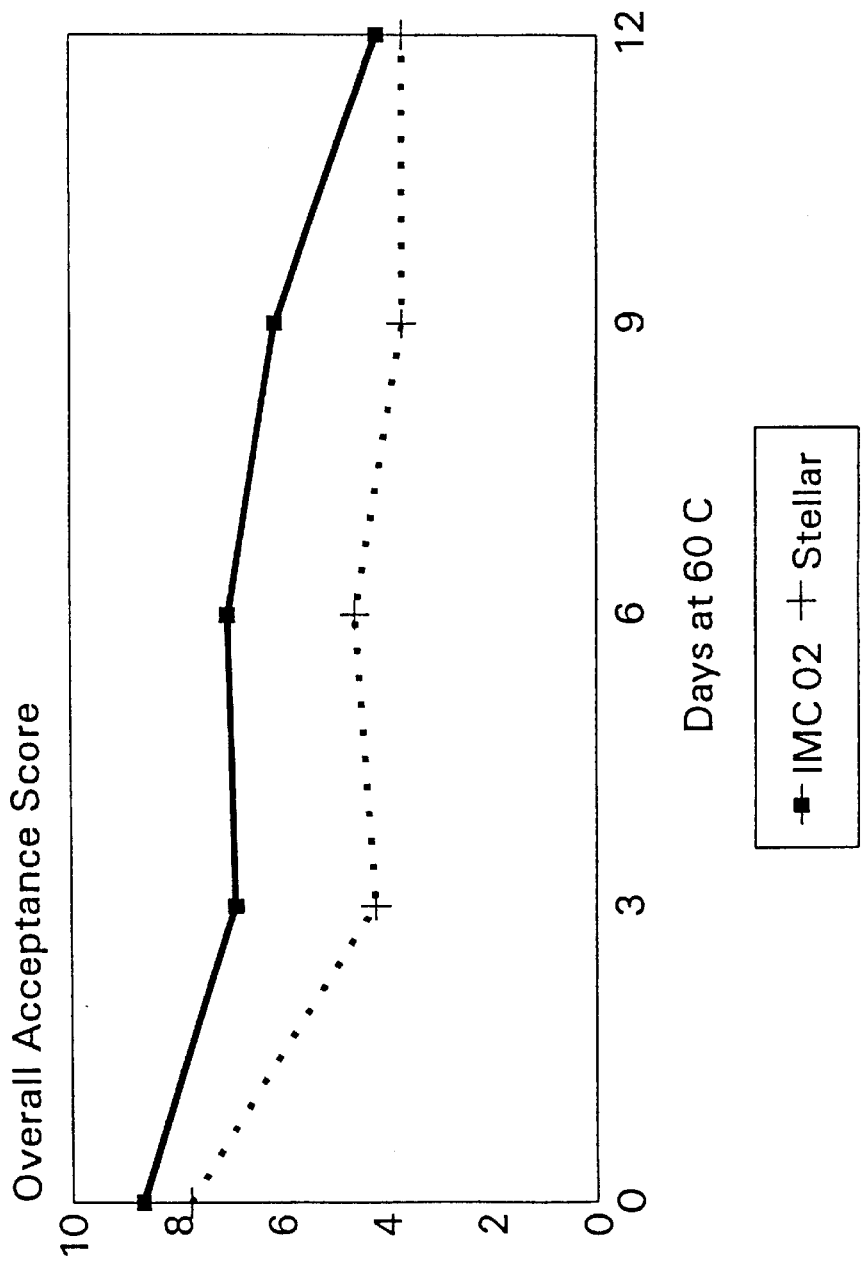
FIG. 8 shows the overall acceptance scores from accelerated aging tests for IMC 02 and Stellar.
Figure 9:
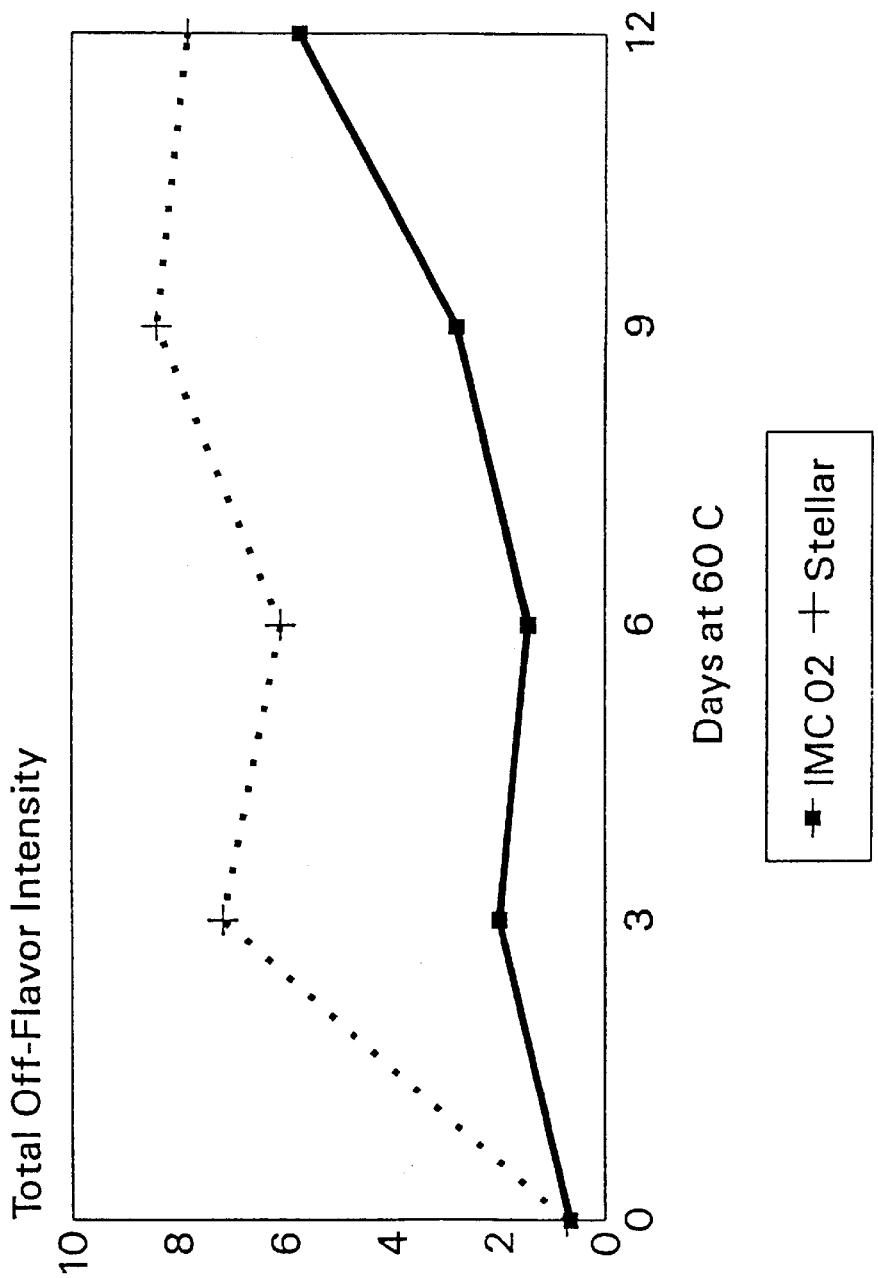
FIG. 9 shows the off-flavor intensity scores from accelerated aging tests for IMC 02 and Stellar.

[1]Overall acceptance scores are based on a 0–9 scale; 0 is extremely unacceptable and 9 is very acceptable.
[2]Total off-flavors include fishy, green, cardboard, plastic and painty. Ratings are based on a 0–15 scale, where 0 is bland and 15 is very intense. (See FIGS. 8 and 9)

Figure 10:
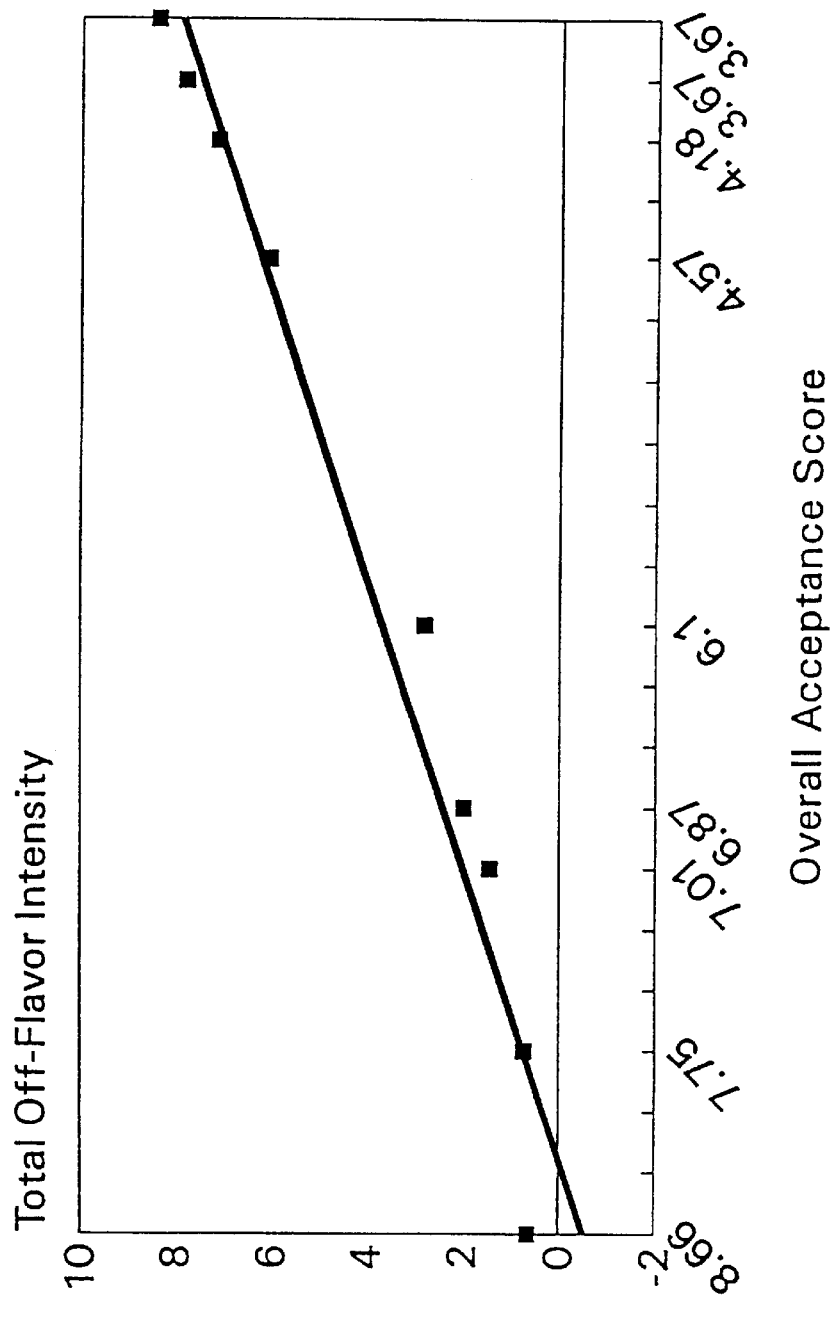
FIG. 10 shows a linear regression analysis for overall acceptance scores versus off-flavor intensity scores for IMC 02 and Stellar.

Results: Overall acceptability scores were significantly different after 0, 6 and 9 days (p=0.05) (see Table XV). Correlation between overall acceptance score and total off-flavor intensities is $r^2$-0.9428 (see FIG. 10).

Significantly lower overall acceptance scores and lower off-flavor intensities indicates IMC 02 has significantly better flavor stability than Stellar.

What is claimed is:

1. A canola oil from Brassica seeds, said oil having an α-linolenic acid content of about 1.7% to about 7% relative to the total fatty acid content, and a sulfur content of less than or equal to 3.0 ppm as determined by high performance liquid chromatography.

2. The oil of claim 1, wherein said α-linolenic acid content is from about 1.9% to about 4.1%.

3. The oil of claim 1, wherein said oil has a sulfur content of about 1.3 ppm as determined by high performance liquid chromatography.

4. The oil of claim 1, said oil having a significantly reduced overall room-odor intensity relative to the overall room-odor intensity of generic canola oil, a significant difference in overall room-odor intensity being indicated by a difference of greater than 1.0 obtained in a standardized sensory evaluation.

5. The oil of claim 4 wherein said oil has, when hydrogenated, a significantly reduced overall room-odor intensity relative to the overall room-odor intensity of hydrogenated generic canola oil.

6. A canola oil from Brassica seeds, said oil having an α-linolenic acid content from about 1.7% to about 7% relative to the total fatty acid content, and wherein said oil has an overall room-odor intensity that is substantially the same throughout said α-linolenic acid content range as determined by a standardized sensory evaluation.

7. The oil of claim 6, wherein said α-linolenic acid content is from about 1.9% to about 4.1%.

8. The oil of claim 1, wherein said oil has a sulfur content of less than or equal to 3.0 ppm as determined by high performance liquid chromatography.

9. A method of producing a canola oil, comprising the steps of:

a) crushing Brassica seeds;

b) extracting a crude oil from said crushed seeds; and c) refining, bleaching and deodorizing said crude oil to produce said canola oil, said canola oil having an α-linolenic acid content of from about 1.7% to about 7% relative to the total fatty acid content and a sulfur content of less than or equal to 3.0 ppm as determined by high performance liquid chromatography.

10. The method of claim 9, wherein said canola oil has an overall room-odor intensity that is substantially the same throughout said α-linolenic acid content range, as determined by a standardized sensory evaluation.

11. The method of claim 9, wherein said α-linolenic acid content is from about 1.9% to about 4.1%.

12. The method of claim 9, wherein said canola oil has a sulfur content of about 1.3 ppm as determined by high performance liquid chromatography.

13. The method of claim 9, wherein said Brassica seeds are produced by a canola plant line designated IMC 01 and having ATCC accession No. 40579, or progeny thereof.

14. A method of producing a canola oil, said method comprising a) crushing Brassica seeds;

b) extracting a crude oil from said crushed seeds; and c) refining, bleaching, and deodorizing said crude oil to produce said canola oil, said canola oil having an α-linolenic acid content from about 1.7% to about 7% relative to the total fatty acid content, and wherein said oil has an overall room-odor intensity that is substantially the same throughout said α-linolenic acid content range as determined by a standardized sensory evaluation.

15. The method of claim 14, wherein said α-linolenic acid content is from about 1.9% to about 4.1%.

16. The method of claim 14, wherein said oil has a sulfur content of less than or equal to 3.0 ppm as determined by high performance liquid chromatography.

17. The method of claim 14, wherein said canola oil has a sulfur content of about 1.3 ppm as determined by high performance liquid chromatography.

18. The method of claim 14, wherein said Brassica seeds are produced by a canola plant line designated IMC 01 and having ATCC accession No. 40579, or progeny thereof.

* * * * *

UNITED STATES PATENT AND TRADEMARK OFFICE
CERTIFICATE OF CORRECTION

PATENT NO.    : 6,270,828 B1
DATED         : August 7, 2001
INVENTOR(S)   : Lorin R. DeBonte, Zhegong Fan and Willie H-T Loh It is certified that error appears in the above-identified patent and that said Letters Patent is hereby corrected as shown below:

<u>Column 18,</u>
Line 37, please delete "claim 1" and insert -- claim 6 -- therefor.

Signed and Sealed this

Fourteenth Day of May, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,270,828 B1
DATED         : August 7, 2001
INVENTOR(S)   : Lorin R. DeBonte, Zhegong Fan and Willie H-T Loh It is certified that error appears in the above-identified patent and that said Letters Patent is hereby corrected as shown below:

<u>Title page,</u>
Item [73], Assignee, please delete "Cargrill" and insert -- Cargill -- therefor.
Item [60], Related U.S. Application Data, after "Division of application No. 08/290,660, filed on Aug. 15, 1994, now Pat. No. 5,750,827, which is a continuation-in-part of application No. 08/140,205, filed on Nov. 12, 1993, now abandoned," please insert -- which claims priority to PCT/US92/08140, filed Sep. 30, 1992, which is a continuation of application Ser. No. 07/767,748, filed Sep. 30, 1991, now abandoned. --

<u>Column 1,</u>
Line 9, please delete "U.S. Pat. No. 5,750,807" and insert -- U.S. Pat. No. 5,750,827 -- therefor.

Signed and Sealed this

Second Day of September, 2003

JAMES E. ROGAN
*Director of the United States Patent and Trademark Office*